(12) United States Patent
Hamann et al.

(10) Patent No.: US 9,242,104 B2
(45) Date of Patent: Jan. 26, 2016

(54) SYSTEMS FOR PATIENT CONTROL OF IMPLANTABLE MEDICAL DEVICE THERAPY

(75) Inventors: Jason J. Hamann, Blaine, MN (US); Stephen Ruble, Lino Lakes, MN (US); Rafael Carbunaru, Valley Village, CA (US); David J. Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 351 days.

(21) Appl. No.: 13/104,635

(22) Filed: May 10, 2011

(65) Prior Publication Data

US 2011/0282416 A1    Nov. 17, 2011

Related U.S. Application Data

(60) Provisional application No. 61/333,589, filed on May 11, 2010.

(51) Int. Cl.
*A61N 1/00* (2006.01)
*A61N 1/372* (2006.01)
*A61N 1/36* (2006.01)

(52) U.S. Cl.
CPC ........ *A61N 1/37247* (2013.01); *A61N 1/36132* (2013.01); *A61N 1/36053* (2013.01); *A61N 1/36114* (2013.01)

(58) Field of Classification Search
CPC ........... A61N 1/36132; A61N 1/36053; A61N 1/36114; A61N 1/37247
USPC ............... 607/7, 11, 14, 15, 17, 59, 62
See application file for complete search history.

(56) References Cited

U.S. PATENT DOCUMENTS 5,205,285 A    4/1993   Baker
5,215,086 A    6/1993   Terry, Jr. et al.
(Continued)

FOREIGN PATENT DOCUMENTS

AU    2011250932 B2    11/2011
CN      101678205 A     3/2010
(Continued)

OTHER PUBLICATIONS

"International Application Serial No. PCT/US2011/035931, International Preliminary Report on Patentability mailed Nov. 22, 2012", 7 pgs.

(Continued)

*Primary Examiner* — Niketa Patel
*Assistant Examiner* — Lindsey G Hankins
(74) *Attorney, Agent, or Firm* — Schwegman Lundberg & Woessner, P.A.

(57) ABSTRACT

Various embodiments provide a method performed by an IMD to deliver a therapy to a patient. In some embodiments of the method, the therapy is delivered to the patient, and a trigger that is controlled by the patient is detected by the IMD. The therapy is automatically interrupted in response to the detected trigger, and is automatically restored after a defined period after the detected trigger. In some embodiments of the method, a trigger that is controlled by the patient is detected. The therapy is automatically initiated in response to the detected trigger, and is automatically stopped after a defined period after the detected trigger.

23 Claims, 10 Drawing Sheets

(56) References Cited

U.S. PATENT DOCUMENTS

| | | | |
|---|---|---|---|
| 5,279,291 A | 1/1994 | Adams et al. | |
| 5,304,206 A | 4/1994 | Baker, Jr. et al. | |
| 5,441,519 A | 8/1995 | Sears et al. | |
| 5,540,730 A | 7/1996 | Terry, Jr. et al. | |
| 5,549,641 A | 8/1996 | Ayers et al. | |
| 5,549,655 A * | 8/1996 | Erickson | 607/42 |
| 6,721,603 B2 | 4/2004 | Zabara et al. | |
| D490,525 S | 5/2004 | Stein et al. | |
| 6,879,859 B1 | 4/2005 | Boveja | |
| 7,162,303 B2 | 1/2007 | Levin et al. | |
| 7,400,928 B2 | 7/2008 | Hatlestsad | |
| 2004/0073093 A1 | 4/2004 | Hatlestad | |
| 2004/0181115 A1* | 9/2004 | Sandyk et al. | 600/9 |
| 2007/0027482 A1 | 2/2007 | Parnis et al. | |
| 2007/0027497 A1 | 2/2007 | Parnis | |
| 2007/0173890 A1 | 7/2007 | Armstrong | |
| 2007/0173891 A1 | 7/2007 | Buras et al. | |
| 2008/0147140 A1 | 6/2008 | Ternes et al. | |
| 2008/0269839 A1* | 10/2008 | Armstrong | 607/59 |
| 2009/0228078 A1 | 9/2009 | Zhang et al. | |
| 2010/0010571 A1 | 1/2010 | Skelton et al. | |
| 2010/0010575 A1* | 1/2010 | Skelton et al. | 607/60 |
| 2010/0106217 A1 | 4/2010 | Colborn | |
| 2014/0228912 A1 | 8/2014 | Seim et al. | |

FOREIGN PATENT DOCUMENTS

| | | |
|---|---|---|
| JP | 06511164 A | 12/1994 |
| JP | 2004537355 A | 12/2004 |
| JP | 2010508969 A | 3/2010 |
| JP | 2010512833 A | 4/2010 |
| JP | 2013526345 A | 6/2013 |

OTHER PUBLICATIONS

"Chinese Application Serial No. 201180032621.2, Office Action mailed May 6, 2014", 32 pgs.

"Japanese Application Serial No. 2013-510244, Office Action mailed Jan. 27, 2014", With English Translation, 9 pgs.

"Chinese Application Serial No. 201180032621.2, Office Action mailed Jan. 6, 2015", 33 pgs.

"Japanese Application Serial No. 2013-510244, Office Action mailed Nov. 4, 2014", 3 pgs.

"Latitude(r) Patient Management System", Boston Scientific Corporation, St. Paul, MN, (2008), 10 pgs.

"Precision Plus tm SCS System with Revolutionary i-Sculpt tm Technology", Boston Scientific, 4 pgs.

"Summary of Safety & Effectiveness Data: Automatic Implantable Cardiac Defibrillator", http://www.accessdata.fda.gov/cdrh__docs/pdf/P960040S028b.pdf, 36 pgs.

"Using a Magnet to Temporarily Inhibit Tachy Therapy or Change Tachy Therapy to Off", Boston Scientific, A Closer look Product Education at a Glance, http://www.bostonscientific.com/templatedata/imports/HTML/CRM/A__Closer__Look/pdfs/ACL__Using__Magnet__Inihibit__Change__Tachy__Therapy__030909.pdf, 2 pgs.

Daoud, Emile G, et al., "Initial Clinical Experience With Ambulatory Use of an Implantable Atrial Defibrillator for Conversion of Atrial Fibrillation", Circulation Journal of The American Heart Association 102, http://circ.ahajournals.org/cgi/reprint/102/12/1407, (2000), 1407-1413.

* cited by examiner

SYSTEMS FOR PATIENT CONTROL OF IMPLANTABLE MEDICAL DEVICE THERAPY

CLAIM OF PRIORITY

This application claims the benefit of priority under 35 U.S.C. §119(e) of U.S. Provisional Patent Application Ser. No. 61/333,589, filed on May 11, 2010, which is herein incorporated by reference in its entirety.

TECHNICAL FIELD

This application relates generally to medical devices and, more particularly, to systems, devices and methods for enabling patient control of implantable medical device therapy.

BACKGROUND

Implantable Medical Devices (IMDs) have been designed or proposed to treat various conditions. For example, some IMDs are designed to treat cardiac conditions and perform functions such as pacing, cardioversion and defibrillation. Some IMDs deliver neural stimulation. By way of example and not limitation, neural stimulation has been proposed as a therapy for respiratory problems such a sleep disordered breathing, blood pressure control such as to treat hypertension, cardiac rhythm management, myocardial infarction and ischemia, heart failure, epilepsy, depression, pain, migraines, eating disorders, obesity, inflammatory diseases, and movement disorders. NeuroCardiac Therapy (NCT), as used herein, refers to neural stimulation delivered for a cardiovascular therapy. NCT, by way of example and not limitation, includes the stimulation of an autonomic neural target to provide a therapy for a cardiac arrhythmia, ischemia, heart failure, angina, atherosclerosis, blood pressure, and the like. By way of example and not limitation, autonomic neural targets used to deliver NCT include the vagus nerve, cardiac branches of the vagal nerves, baroreceptors, chemoreceptors, cardiac fat pads, the spinal column or some nerve roots extending from the spinal column.

Some current and proposed neural stimulation therapies are delivered for periods on the order of minutes, days, weeks, months or years. If the neural stimulation therapy is associated with an undesired response, the chronic nature of the therapy may exacerbate the undesirability of the response, as it can have long-term consequences for the health or quality of life for the patient. NCT, as currently envisioned, has side effects that may be occasionally intolerable or inconvenient. For example, the therapy may change heart rate and blood pressure at undesirable times. Other examples of side effects involve the laryngeal vibration or cough attributed to vagal nerve stimulation.

SUMMARY

Various embodiments provide a method performed by an IMD to deliver a therapy to a patient. In some embodiments of the method, the therapy is delivered to the patient, and a trigger that is controlled by the patient is detected by the IMD. The therapy is automatically interrupted in response to the detected trigger, and is automatically restored after a defined period after the detected trigger. In some embodiments of the method, a trigger that is controlled by the patient is detected. The therapy is automatically initiated in response to the detected trigger, and is automatically stopped after a defined period after the detected trigger. According to various embodiments, automatically interrupting the therapy includes automatically stopping the therapy in response to the detected trigger, or automatically adjusting an intensity of the therapy in response to the detected trigger.

Various embodiments provide an IMD for implantation in a patient. Some IMD embodiments include a neural stimulation circuit configured for use to deliver a neural stimulation therapy to the patient, and a controller, where the controller is configured to control the neural stimulator to deliver the neural stimulation therapy, detect a trigger that is controlled by the patient, automatically interrupt the therapy in response to the detected trigger, and automatically restore the therapy after a defined period after the detected trigger. Some IMD embodiments include a neural stimulation circuit configured for use to deliver a neural stimulation therapy to the patient, and a controller, where the controller is configured to detect a trigger that is controlled by the patient, automatically initiate the therapy in response to the detected trigger, and automatically stop the therapy after a defined period after the detected trigger.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter provides patient control over the neural stimulation therapies such as NCT. It is believed that, by increasing patient control, the present subject matter increases patient acceptance and compliance. The present subject matter generally relates to neural stimulation therapies. Some embodiments relate to autonomic neural stimulation therapies, and some embodiments relate to NCT. NCT may provide a cardiovascular therapy by stimulating parasympathetic activity, inhibiting parasympathetic activity, stimulating sympathetic activity, or inhibiting sympathetic activity.

Figure 1:
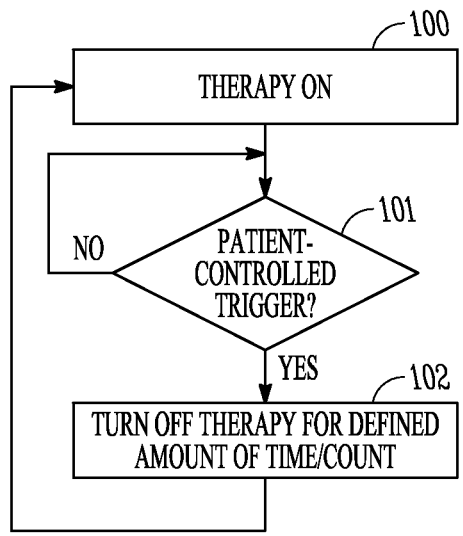
FIGS. 1-4 illustrate various embodiments of a method performed by an implantable medical device to deliver a therapy to a patient.

As generally illustrated in FIG. 1, various embodiments of the present subject matter provide a system configured to receive a patient-controlled trigger, and respond by temporarily suspending therapy of an implanted medical device, followed by automatic resumption of therapy after a defined time interval or count. For example, the patient can trigger the device to suspend therapy if the side effects are intolerable or inconvenient. Thus, for example, if the patient is unable to deliver a speech or fall asleep because of the NCT, the patient can disable the NCT to allow the patient to deliver the speech or to fall asleep. The device automatically resumes therapy after a defined time period. If therapy side effects are no longer intolerable or inconvenient, it is expected that the patient will allow the therapy to continue. As patient interaction is not required to resume the NCT after the defined length of time, patient forgetfulness or inactivity will not detrimentally affect therapy compliance.

FIG. 1 illustrates an embodiment of a method performed by an implantable medical device to deliver a therapy to a patient. The neural stimulation therapy (e.g. NCT) is on at 100. The therapy may be delivered according to programmed schedule. For example, NCT may be delivered as bursts of neural stimulation pulses, where each burst starts at a programmed time and lasts for a programmed time. The bursts may be separated by a programmed duration without any neural stimulation. At 101, it is determined whether the patient-controlled trigger has been received. If the trigger has not been received, the therapy is continued to be delivered according to its normal routine (e.g. programmed schedule). If the trigger is received, the therapy is turned OFF or disabled for a defined amount of time/count, as generally illustrated at 102. After the defined amount of time/count, the therapy automatically resumes according to its normal routine or programmed schedule.

Figure 2:
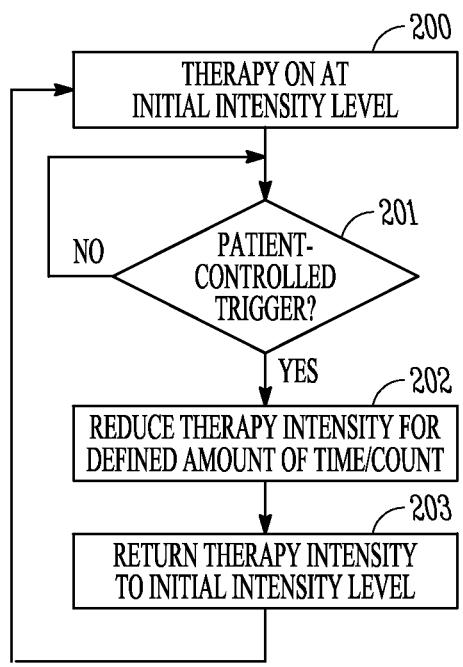

As generally illustrated in FIG. 2, various embodiments of the present subject matter provide a system configured to receive a patient-controlled trigger and respond by temporarily reducing a therapy intensity of an implanted medical device, followed by automatic return back to the initial therapy intensity after a defined time interval. By way of example and not limitation, some embodiments temporarily reduce an amplitude, a duty cycle of the neural stimulation pulses, or the duration of the neural stimulation bursts in response to the trigger, and then automatically restore stimulation, after a defied amount of time/count, to the value before the trigger. FIG. 2 illustrates an embodiment of a method performed by an implantable medical device to deliver a therapy to a patient. The neural stimulation therapy (e.g. NCT) is on at 200. The therapy may be delivered according to programmed schedule, for example. At 201, it is determined whether the patient-controlled trigger has been received. If the trigger has not been received, the therapy is continued to be delivered according to its normal routine (e.g. programmed schedule). If the trigger is received, the therapy intensity is reduced for a defined amount of time/count, as generally illustrated at 202. After the defined amount of time/count, the therapy intensity is returned to the normal or initial intensity level, as illustrated at 203, and the therapy continues at 200. The return to the normal or initial intensity level may be performed in one or more stages, or may be performed as a step function or as a gradual adjustment back to the normal or initial intensity level.

Some embodiments provide one or more indications, such as sound, vibration, command to external receiver, and the like, that the NCT is about to be resumed unless retriggered. Some embodiments monitor the number of patient-controlled trigger events. If the number of trigger events exceeds a defined number, then the device permanently turns the NCT OFF or permanently reduces the intensity of the NCT until the NCT is reset by a clinician.

Figure 3:
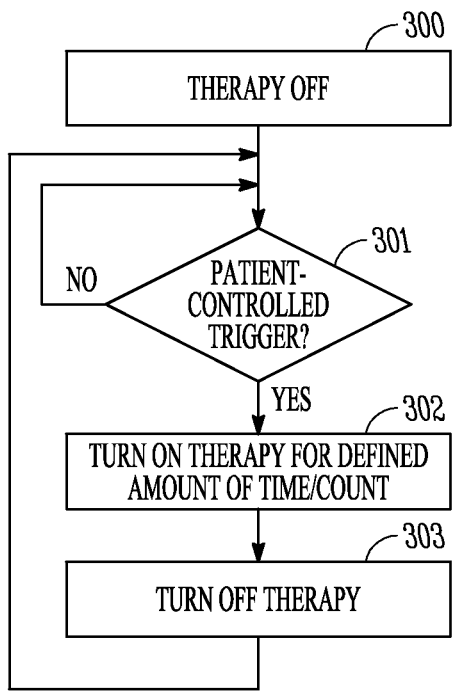

As generally illustrated in FIG. 3, various embodiments of the present subject matter provide a system configured to receive a patient-controlled trigger and respond by temporarily enabling therapy of an implanted medical device followed by automatic disabling of therapy after a defined time interval. For example, the patient can trigger the device to initiate a therapy of a defined time interval, when the patient determines that it is an appropriate or convenient time for the therapy. For example, if NCT is only needed for a limited amount of time each day, the patient can control when therapy is delivered, such as in the evening just prior to going to bed, or after a meal or drink, or after taking other medicine such as an ACE inhibitor. The device automatically disables therapy after the defined time period, until such time that the patient attempts to retrigger the device to reinitiate the therapy. FIG. 3 illustrates an embodiment of a method performed by an implantable medical device to deliver a therapy to a patient. The neural stimulation therapy (e.g. NCT) is OFF at 300. At 301, it is determined whether the patient-controlled trigger has been received. If the trigger has not been received, the therapy remains OFF. If the trigger is received, the therapy is turned ON for a defined amount of time/count, as generally illustrated at 302. After the defined amount of time/count, the therapy is turned off, as illustrated at 303, and the process returns to 301 to determine if another patient-controlled trigger has been received.

Figure 4:
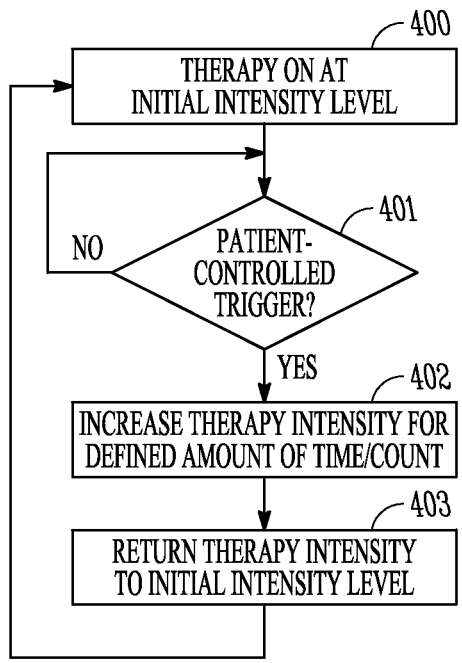

As generally illustrated in FIG. 4, various embodiments of the present subject matter provide a system configured to receive a patient-controlled trigger to temporarily increase a therapy intensity of an implanted medical device, followed by automatic return back to the initial therapy intensity after a defined time interval. By way of example and not limitation, some embodiments temporarily increase amplitude or duty cycle for a determined period of time in response to the trigger, and then automatically restore the amplitude or the duty cycle to the value before the trigger. FIG. 4 illustrates an embodiment of a method performed by an implantable medical device to deliver a therapy to a patient. The neural stimulation therapy (e.g. NCT) is ON at an initial intensity level, as illustrated at 400. The therapy may be delivered according to programmed schedule, for example. At 401, it is determined whether the patient-controlled trigger has been received. If the trigger has not been received, the therapy is continued to be delivered according to its normal intensity. If the trigger is received, the therapy intensity is increased for a defined amount of time/count, as generally illustrated at 402. After the defined amount of time/count, the therapy intensity is returned to the normal or initial intensity level, as illustrated at 403, and the therapy continues at 400. The return to the normal or initial intensity level may be performed in one or more stages, or may be performed as a step function or as a gradual adjustment back to the normal or initial intensity level.

Some device embodiments provide one or more indications, such as sound, vibration, command to external receiver, and the like, that the NCT is about to be turned off or resumed at normal intensity levels. Some embodiments monitor the number of patient-controlled trigger events. If the number of trigger events exceeds a defined number, then the device permanently turns the NCT ON or permanently increases the intensity of the NCT until the NCT is reset by a clinician.

Some embodiments decrement a timer or a counter. Some of these embodiments inhibit the NCT as long as the timer is non-zero, and some of these embodiments provide the NCT as long as the time is non-zero. The timer or counter may be based on time, cardiac cycles, neural cycles, and the like. The neural cycles may be based on the number of stimulation pulses, or the number of bursts of multiple pulses, by way of example.

Some embodiments use a counter to count the patient-controlled triggers. If the number of trigger events exceeds a defined number, then according to some embodiments, the device permanently turns the NCT ON to deliver the NCT according to a programmed schedule. Some embodiments are configured to permanently turn the NCT OFF if the number of trigger events exceeds a defined number. Some embodiments turn the NCT ON whenever the therapy delivering device is in presence of a patient-controlled trigger, and some embodiments turn the NCT OFF whenever the therapy delivering device is in the presence of a patient-controlled trigger.

For example, if the counter indicates that there has been more than a defined number of triggers over a defined period of time or number of counts, some embodiments override the therapy until an authorized individual intervenes. For example, some embodiments disable the therapy until a clinician intervenes and resets or reprograms the therapy. In another embodiment, the system is configured to respond to a defined number of trigger events over a defined period of time or number of counts by disabling therapy for a determined period of time before being enabled without intervention by the authorized individual. For example, if a defined number of triggers occur over a defined period of time or number of counts, the NCT can be disabled for a day or for a few days. Thus, for example, the NCT can be disabled without a programmer to accommodate emergencies, surgery, and the like. Some embodiments ladder the response strategy. For example, a first trigger may cause the therapy to be disabled for a short time period, a second trigger within a defined period may cause the therapy to be disabled for a second time period longer than the first, and a third time period may cause the therapy to be disabled until a clinician intervenes.

Some embodiments enforce a therapy dose. For example, some embodiments incorporate a timer or counter that automatically re-enables the NCT after a period of time or count and prevents disabling again until therapy has been continuously delivered for a minimum period of time. These embodiments enforce a minimum amount of daily therapy (or therapy over another period of time). Thus, if a certain amount of therapy over a period of time is required to be effective, these embodiments can be used to positively confirm that the amount of the therapy that is being delivered is effective.

The present subject matter includes devices that are configured to receive a patient-controlled trigger. Examples of patient-controlled triggers include a magnet, a handheld programmer that communicates using telemetry or RF signals, a key fob, a communicator button such as the LATITUDE communicator button, and a switch on the housing of the implantable medical device configured to be switched by the patient by pressing on the button. A key fob, for example, is a hardware device with built-in authentication mechanism. In an embodiment, a user enters a personal identification number (PIN) into the key fob to authenticate the user, and the key fob displays or otherwise provides a number or character string that the user can use to access the implantable medical device. Some embodiments use a general patient control such as a magnet, and other embodiments use a patient control associated with a specific device such as an encrypted serial number handshake. Rather than using a magnet or RF signals, some embodiments allow a patient to directly activate the NCT delivered by the implantable medical device using button press.

Figure 5:
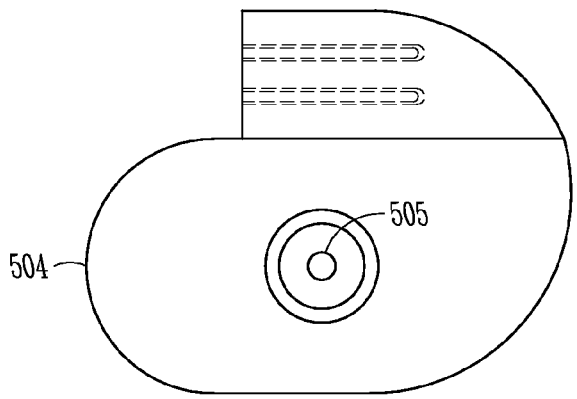
FIG. 5 illustrates an embodiment of an implantable pulse generator with a switch on the can that can be manually actuated when implanted.

FIG. 5 illustrates an embodiment of an implantable pulse generator with a switch on the can that can be pressed directly without the involvement of any other additional object. The implantable medical device includes a hermetically sealed can 504 to house its circuit. The can 504 includes a button or other manually actuated switch 505 positioned on a surface of the can closest to the skin of the patient. Since the can is implanted subcutaneously, (over the muscle and beneath the skin, the patient can press against his or her skin to actuate the switch, and thus provide the patient-controlled trigger.

Various embodiments provide individual application hysteresis, to account for situations where the patient controlled trigger is triggered more than once in a relatively short time frame. For example, some system embodiments are configured to disable therapy until re-enabled by an authorized person when three triggers occur within a 24 hour period. If triggers occur at 1:02.00 AM, 7:10.32.0 PM and 7:10.32.1 PM, some system embodiments are configured to ignore the 7:10.32.1 PM trigger, assuming that the patient only meant to trigger the system once. Some embodiments implement the hysteresis as a programmable debounce period. Some system embodiments are programmed with longer debounce periods that allow the system to confirm that the patient is providing the trigger as a response to different episodes.

In addition to the patient-controlled input, some embodiments control whether the NCT is OFF or ON based on additional input, such as weight, blood pressure, and answers to questions related to medications and diet. Some embodiments communicate directly to devices that measure the patient input. Some embodiments communicate with a patient communicator, such as a LATITUDE communicator, to receive information from the patient.

Some embodiments deliver NCT according to a therapy schedule that establishes semi-permanent periodic therapy start and end times. This allows the NCT to be delivered one hour a day, eight hours a day, or according to some other schedule. The patient-controlled trigger can be used to modify the scheduled therapy. For example, some embodiments remember when the last patient trigger occurred, and modify the NCT schedule accordingly. For example, if the last patient trigger occurred at 10:43 PM, some embodiments will begin to initiate therapy immediately for a therapy duration of 8 hours, and will begin therapy every day after at 10:43 PM for eight hours without further patient interaction. Some embodiments establish consistent periods of therapy (either therapy ON or therapy OFF). This, for example, can assist a patient who may encounter NCT-induced dysphagia by creating therapy OFF periods around typical breakfast, lunch and dinner times. By way of another example, a patient may have his or her voice altered by the NCT. If this patient consistently attended a 9 AM weekday mass, the device would establish this as a consistent time to disable therapy during the mass. Various embodiments limit the number of allowable OFF times per day (or other defined period of time) based on what research established as necessary for effective therapy.

Some system embodiments are configured to implement more than one therapy in a concurrent or integrated manner. Some system embodiments are configured to respond to the patient controlled input to temporarily turn on or off or otherwise modify one of the therapies but not the other therapy or therapies. Some system embodiments are configured to respond to the patient controlled input to temporarily turn on or off or otherwise modify a subset of the concurrently delivered therapies but not all of the therapies. Some system embodiments are configured to respond to the patient controlled input to temporarily turn on or off or otherwise modify all of the therapies delivered by the device.

Figure 6:
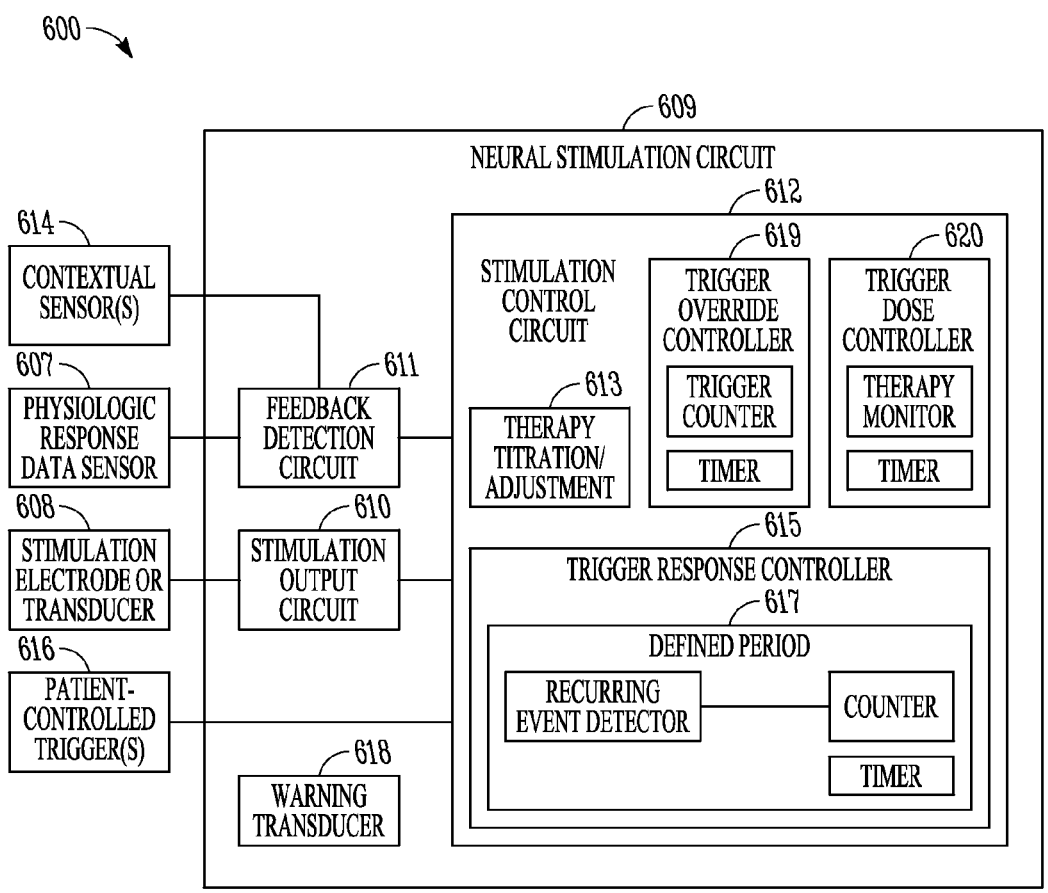
FIG. 6 is a block diagram illustrating an embodiment of a circuit of a neural stimulation system.

FIG. 6 is a block diagram illustrating an embodiment of a circuit of a neural stimulation system 606. The system 606 includes a data sensor 607 adapted to sense a physiologic response to the neural stimulation, a stimulation electrode/transducer 608, and a neural stimulation circuit 609. The neural stimulation circuit 609 includes a stimulation output circuit 610, a feedback detection circuit 611, and a stimulation control circuit 612. The stimulation control circuit 612 controls the delivery of the neural stimulation pulses and includes a therapy titration adjustment circuit or module 613. The stimulation output circuit 610 delivers the neural stimulation pulses upon receiving a pulse delivery signal from stimulation control circuit 612. The data sensor 607 provides signals indicative of a physiological response to the applied neural stimulation. A feedback detection circuit 611 receives the signal indicative of the response and processes the signal to provide a neural stimulation feedback signal. In various embodiments, the response includes a cardiac activity such as heart rate, HRV, HRT, PR interval, T-wave velocity, or action potential duration. In various embodiments the response includes a non-cardiac response such as respiration or blood pressure. In various embodiments, the response includes a QT interval or atrial/ventricular refractory periods. In some embodiments, the therapy titration/adjustment module 613 uses the feedback signal to modulate or titrate the therapy generated by the stimulation output circuit 610 to provide the desired physiologic response (e.g. cardiac response or non-cardiac response). Some embodiments include contextual sensor(s) or input(s) 614 connected to the feedback detection circuit 611 to provide a more complete picture of a patient's physiology. The feedback detection circuit can provide the neural stimulation feedback signal based on the physiological response data sensor(s) 607 and the contextual input(s) 614. The contextual input(s) can be used to avoid incomplete data from affecting the neural stimulation. Examples of contextual inputs include an activity sensor, a posture sensor and a timer. Another example of a contextual input is an input that is indicative of a patient's environment (e.g. in bedroom or car). Any one or combination of two or more contextual inputs can be used by the feedback detection circuit. For example, an elevated heart rate may be representative of exercise rather than a reason for titrating the neural stimulation therapy.

The illustrated stimulation control circuit 612 includes a trigger response controller 615, which is configured to respond to a patient-controlled trigger 616. The stimulation and control circuit also includes at least one timer or counter, used to determine the defined period 617 for responding to the trigger. The counter can be used to count detected recurring events, such as events in a cardiac cycle or neural stimulation pulses. When the defined period 617 after the trigger ends, some embodiments use the warning transducer 618 to warn the patient that the therapy will automatically resume. The warning transducer 618 may vibrate, produce an audible alert, or otherwise provide a signal that is discernible to the patient.

The illustrated stimulation control circuit 612 also includes an override controller 619 and a therapy dose controller 620. The illustrated override controller 619 includes a trigger counter and a timer, and is configured to count a number of detected triggers over a defined period, compare the number of detected triggers over the defined period to a defined number of triggers, and automatically interrupt the therapy until an authorized individual resets the therapy when the number of detected triggers over the defined period reaches the defined number of triggers. The illustrated therapy dose controller 620 includes a therapy monitor and a timer, and is configured to determine an amount of the therapy over a defined therapy window, compare the amount of the therapy over the defined therapy window to a defined therapy amount, and change the response to the trigger if the amount of the therapy over the defined therapy window is less than the defined therapy amount.

Figure 7:
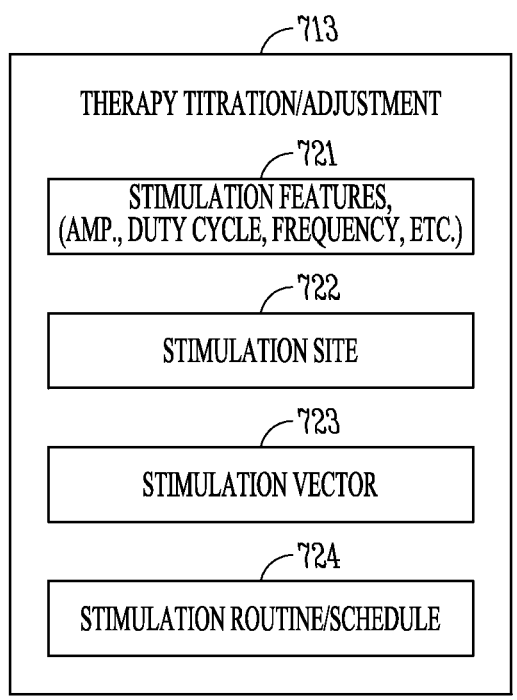
FIG. 7 illustrates an embodiment of a therapy titration module such as is illustrated in FIG. 6.

FIG. 7 illustrates an embodiment of a therapy titration module 713 such as is illustrated at 613 in FIG. 6. According to various embodiments, the stimulation control circuit is adapted to set or adjust any one or any combination of stimulation features 721. Examples of stimulation features include the amplitude, frequency, polarity and wave morphology of the stimulation signal. Examples of wave morphology include a square wave, triangle wave, sinusoidal wave, and waves with desired harmonic components to mimic naturally-occurring baroreflex stimulation. Some embodiments of the stimulation output circuit are adapted to generate a stimulation signal with a predetermined amplitude, morphology, pulse width and polarity, and are further adapted to respond to a control signal from the controller to modify at least one of the amplitude, wave morphology, pulse width and polarity. Some embodiments of the neural stimulation circuitry are adapted to generate a stimulation signal with a predetermined frequency, and are further adapted to respond to a control signal from the controller to modify the frequency of the stimulation signal.

The therapy titration module 713 can be programmed to change stimulation sites 722, such as changing the stimulation electrodes used for a neural target or changing the neural targets for the neural stimulation. For example, different electrodes of a multi-electrode cuff can be used to stimulate a neural target. Examples of neural targets include the right and left vagus nerves, cardiac branches of the vagus nerve, cardiac fats pads, baroreceptors, the carotid sinus, the carotid sinus nerve, and the aortic nerve. Autonomic neural targets can include afferent pathways and efferent pathways and can include sympathetic and parasympathetic nerves. The stimulation can include stimulation to stimulate neural traffic or stimulation to inhibit neural traffic. Thus, stimulation to evoke a sympathetic response can involve sympathetic stimulation and/or parasympathetic inhibition; and stimulation to evoke a parasympathetic response can involve parasympathetic stimulation and/or sympathetic inhibition.

The therapy titration module 723 can be programmed to change stimulation vectors 723. Vectors can include stimulation vectors between electrodes, or stimulation vectors for transducers. For example, the stimulation vector between two electrodes can be reversed. One potential application for reversing stimulation vectors includes changing from stimulating neural activity at the neural target to inhibiting neural activity at the neural target. More complicated combinations of electrodes can be used to provide more potential stimulation vectors between or among electrodes. One potential stimulation vector application involves selective neural stimulation (e.g. selective stimulation of the vagus nerve) or changing between a selective stimulation and a more general stimulation of a nerve trunk.

The therapy titration module 713 can be programmed to control the neural stimulation according to stimulation instructions, such as a stimulation routine or schedule 724, stored in memory. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow a more complicated schedule. The programmed pattern of bursts can be more complicated, composed of multiple burst durations and burst interval sequences. The programmed pattern of bursts can be characterized by a duty cycle, which refers to a repeating cycle of neural stimulation ON for a fixed time and neural stimulation OFF for a fixed time. Duty cycle is specified by the ON time and the cycle time, and thus can have units of ON time/cycle time. According to some embodiments, the control circuit controls the neural stimulation generated by the stimulation circuitry by initiating each pulse of the stimulation signal. In some embodiments, the stimulation control circuit initiates a stimulation signal pulse train, where the stimulation signal responds to a command from the controller circuitry by generating a train of pulses at a predetermined frequency and burst duration. The predetermined frequency and burst duration of the pulse train can be programmable. The pattern of pulses in the pulse train can be a simple burst pattern with one burst duration and burst interval or can follow a more complicated burst pattern with multiple burst durations and burst intervals. In some embodiments, the stimulation control circuit controls the stimulation output circuit to initiate a neural stimulation session and to terminate the neural stimulation session. The burst duration of the neural stimulation session under the control of the control circuit can be programmable. The controller may also terminate a neural stimulation session in response to an interrupt signal, such as may be generated by one or more sensed parameters or any other condition where it is determined to be desirable to stop neural stimulation.

A device may include a programmed therapy schedule or routine stored in memory and may further include a clock or timer which can be used to execute the programmable stimulation schedule. For example, a physician can program a daily/weekly schedule of therapy based on the time of day. A stimulation session can begin at a first programmed time, and can end at a second programmed time. Various embodiments initiate and/or terminate a stimulation session based on a signal triggered by a user. Various embodiments use sensed data to enable and/or disable a stimulation session.

According to various embodiments, the stimulation schedule refers to the time intervals or period when the neural stimulation therapy is delivered. A schedule can be defined by a start time and an end time, or a start time and a duration. Various schedules deliver therapy periodically. By way of example and not limitation, a device can be programmed with a therapy schedule to deliver therapy from midnight to 2 AM every day, or to deliver therapy for one hour every six hours, or to deliver therapy for two hours per day, or according to a more complicated timetable. Various device embodiments apply the therapy according to the programmed schedule contingent on enabling conditions, such as sensed exercise periods, patient rest or sleep, low heart rate levels, and the like. For example, the stimulation can be synchronized to the cardiac cycle based on detected events that enable the stimulation. The therapy schedule can also specify how the stimulation is delivered.

Figure 8:
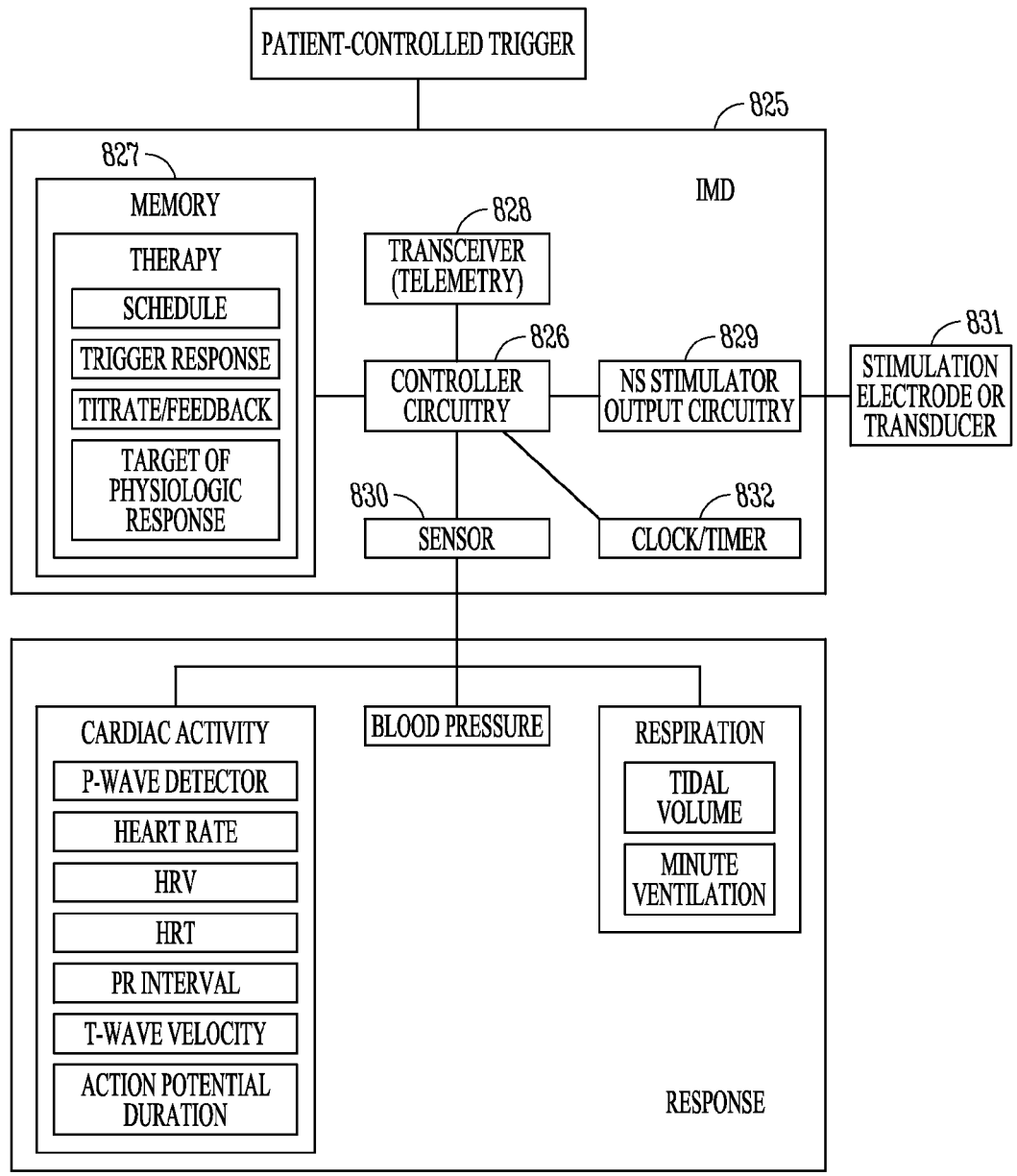
FIG. 8 illustrates an IMD, according to various embodiments of the present subject matter.

FIG. 8 illustrates an IMD, according to various embodiments of the present subject matter. The illustrated IMD 825 provides neural stimulation signals for delivery to predetermined neural targets. The illustrated device includes controller circuitry 826 and memory 827. The controller circuitry is capable of being implemented using hardware, software, and combinations of hardware and software. For example, according to various embodiments, the controller circuitry includes a processor to perform instructions embedded in the memory to perform functions associated with the neural stimulation therapy. The illustrated device further includes a transceiver 828 and associated circuitry for use to communicate with a programmer or another external or internal device. Various embodiments have wireless communication capabilities. For example, some transceiver embodiments use a telemetry coil to wirelessly communicate with a programmer or another external or internal device.

The illustrated device further includes neural stimulation output circuitry 829 and sensor circuitry 830. According to some embodiments, one or more leads are able to be connected to the sensor circuitry and neural stimulation circuitry. Some embodiments use wireless connections between the sensor(s) and sensor circuitry, and some embodiments use wireless connections between the stimulator circuitry and electrodes. According to various embodiments, the neural stimulation circuitry is used to apply electrical stimulation pulses to desired neural targets, such as through one or more stimulation electrodes 831 positioned at predetermined location(s). Some embodiments use transducers to provide other types of energy, such as ultrasound, light or magnetic energy. In various embodiments, the sensor circuitry is used to detect physiological responses. Examples of physiological responses include cardiac activity such as heart rate, HRV, PR interval, T-wave velocity, and action potential duration. Other examples of physiological responses include hemodynamic responses such as blood pressure, and respiratory responses such as tidal volume and minute ventilation. The controller circuitry can control the therapy provided by the system using a therapy schedule and a therapy titration routine in memory 827, or can compare a target range (or ranges) of the sensed physiological response(s) stored in the memory 8xx to the sensed physiological response(s) to appropriately adjust the intensity of the neural stimulation/inhibition.

Some embodiments are adapted to change a stimulation signal feature, the neural stimulation target and/or change the neural stimulation vector as part of a neural stimulation titration routine. According to various embodiments using neural stimulation, the stimulation output circuitry 829 is adapted to set or adjust any one or any combination of stimulation features based on commands from the controller 826. Examples of stimulation features include the amplitude, frequency, polarity and wave morphology of the stimulation signal. Some embodiments are adapted to generate a stimulation signal with a predetermined amplitude, morphology, pulse width and polarity, and are further adapted to respond to a control signal from the controller to modify at least one of the amplitude, wave morphology, pulse width and polarity. Some embodiments are adapted to generate a stimulation signal with a predetermined frequency, and are further adapted to respond to a control signal from the controller to modify the frequency of the stimulation signal.

The controller 826 can be programmed to control the neural stimulation delivered by the stimulation output circuitry 829 according to stimulation instructions, such as a stimulation schedule, stored in the memory 827. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow a more complicated schedule. The programmed pattern of bursts can be more complicated, composed of multiple burst durations and burst interval sequences. The programmed pattern of bursts can be characterized by a duty cycle, which refers to a repeating cycle of neural stimulation ON for a fixed time and neural stimulation OFF for a fixed time.

According to some embodiments, the controller 826 controls the neural stimulation generated by the stimulation circuitry by initiating each pulse of the stimulation signal. In some embodiments, the controller circuitry initiates a stimulation signal pulse train, where the stimulation signal responds to a command from the controller circuitry by generating a train of pulses at a predetermined frequency and burst duration. The predetermined frequency and burst duration of the pulse train can be programmable. The pattern of pulses in the pulse train can be a simple burst pattern with one burst duration and burst interval or can follow a more complicated burst pattern with multiple burst durations and burst intervals. In some embodiments, the controller 826 controls the stimulator output circuitry 829 to initiate a neural stimulation session and to terminate the neural stimulation session. The burst duration of the neural stimulation session under the control of the controller 826 can be programmable. The controller may also terminate a neural stimulation session in response to an interrupt signal, such as may be generated by one or more sensed parameters or any other condition where it is determined to be desirable to stop neural stimulation.

The sensor circuitry is used to detect a physiological response. The detected response can be cardiac activity or surrogates of cardiac activity such as blood pressure and respiration measurements. Examples of cardiac activity include a P-wave and heart rate. The controller 826 compares the response to a target range stored in memory, and controls the neural stimulation based on the comparison in an attempt to keep the response within the target range. The target range can be programmable. According to various embodiments, the controller is configured to respond appropriately to the patient control trigger.

The illustrated device includes a clock or timer/counter 832 which can be used to execute the programmable stimulation schedule. For example, a physician can program a daily schedule of therapy based on the time of day. A stimulation session can begin at a first programmed time, and can end at a second programmed time. Various embodiments initiate and/or terminate a stimulation session based on a signal triggered by a user. Various embodiments use sensed data to enable and/or disable a stimulation session.

The illustrated memory includes a schedule. According to various embodiments, the schedule refers to the time intervals or period when the neural stimulation therapy is delivered. Various device embodiments apply the therapy according to the programmed schedule contingent on enabling conditions, such as poor glucose control, patient rest or sleep, low heart rate levels, and the like. The illustrated memory includes a titration feedback routine and a patient-controlled trigger response routine, which are used by the controller to control the timing and adjustments of neural stimulation generated by the neural stimulator output circuitry. The controller is configured to implement the programmed trigger response routine to provide a desired response to receiving a patient controlled-trigger.

In some embodiments, the therapy is OFF whenever the therapy delivering device is in the presence of a patient controlled trigger. By way of example, the trigger may be a magnet, a communicator such as a LATITUDE communicator telemetry, a specialized pillow, and the like.

Figure 9:
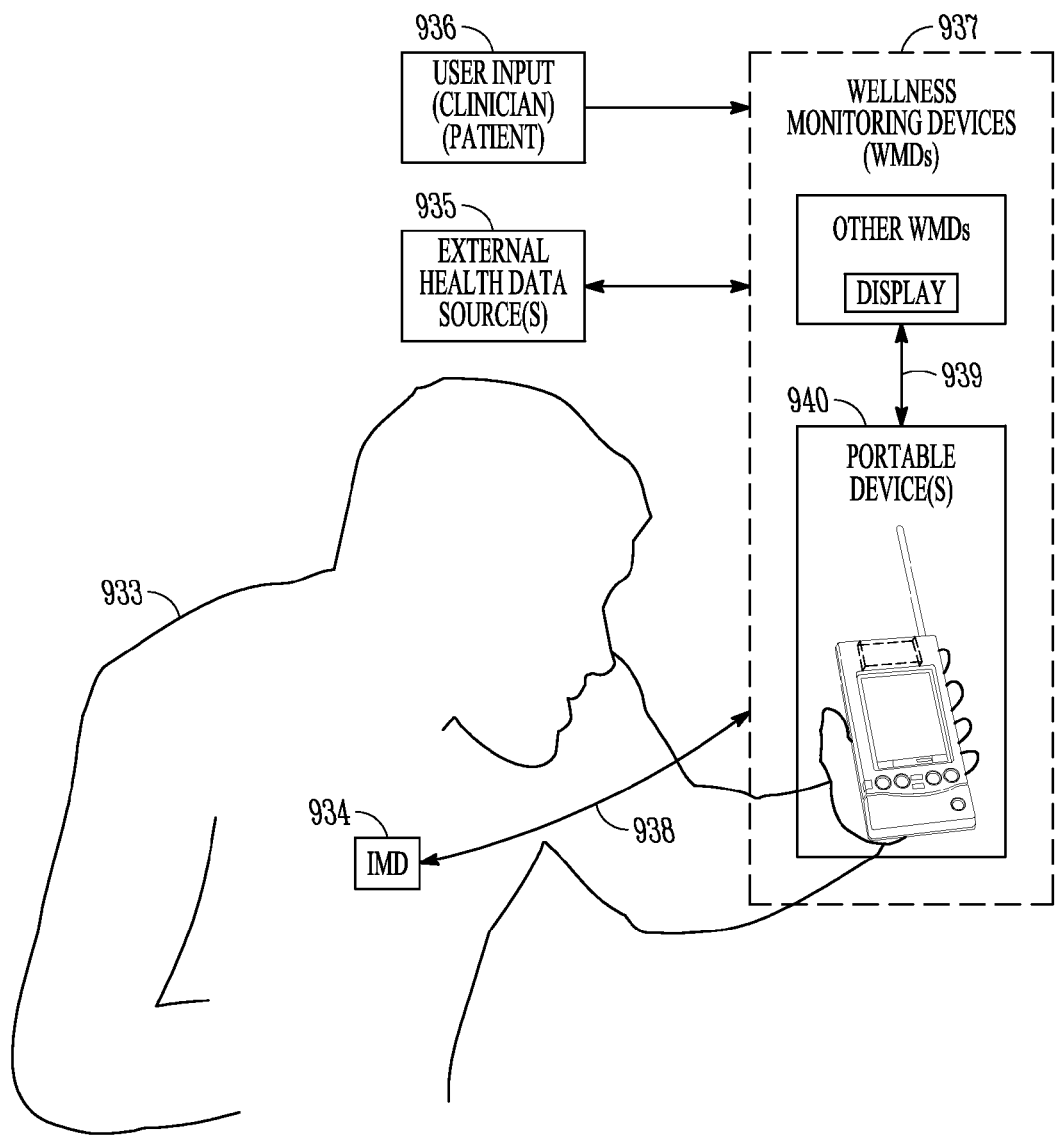
FIG. 9 illustrates a patient management system according to various embodiments of the present subject matter.

FIG. 9 illustrates a patient management system according to various embodiments of the present subject matter. The illustrated system can be used to provide patient-controlled triggers, contextual information, and intervention by an authorized individual such as a clinician. A patient 933 is illustrated with an IMD 934. In various embodiments, the IMD is configured to deliver a neural stimulation therapy such as NCT. The IMD can sense internal parameters. The illustrated system also includes one or more external data source(s) 935 that provide health-related parameters. The external health-related parameters supplement the internal parameters and/or provide a diagnostic context to the internal health-related parameters. Examples of external source(s) of health data include: weight scales, external sensing devices such as body temperature thermometers, blood pressure monitors, and the like; room temperature thermometers, light sensors and the like; databases such as patient history databases that are found in hospitals or clinics and that may include information such as medical test results and family history; a web server database (a database accessible through a global communication network—e.g. Internet) that may include information regarding environment, medication interaction, and the like; databases and/or user inputs; and other external data sources capable of providing health-related parameters.

The illustrated system also includes a user input 936 through which a user is able to input additional health-related parameters for use by a wellness monitoring device (WMD) 937. In various embodiments, the user input 936 includes a touch screen on a PDA or other device, a keyboard and mouse on a computer, and the like. In various embodiments, a patient is able to input additional health-related parameters for use by the wellness monitoring device. In various embodiments, a clinician is able to input additional health-related parameters for use by the WMD.

The WMD 937 is illustrated by a dotted line, and includes one or more devices. In various embodiments, the at least one IMD 934 communicates wirelessly with at least one WMD 937, as shown by communication link 938. In various embodiments that include multiple WMDs, the WMDs are able to communicate with each other, as shown via communication link 939. In various embodiments, the WMD(s) includes portable devices 940 that are external to the body of patient such as a PDA, (variously referred to as a personal digital, or data, assistant), a portable telephone (including a cellular telephone or a cordless telephone), a pager (one way or two way), a handheld, palm-top, laptop, portable or notebook computer, or other such battery operated portable communication device. In various embodiments, the WMD(s) includes programmers. In various embodiments, the WMD(s) includes various non-portable devices such as larger computers or computer enterprise systems.

Depending on the application executing on the portable device 940, the display screen may provide prompts, messages, questions, or other data designed to elicit an input from the patient. In various embodiments, the user input data may be received from a user based on a prompt provided to the user, on an ad hoc basis as determined by the user, or as determined by a processor. The user may enter data using a menu based system, a graphical user interface (GUI), textual data or numerical data.

The trigger may be stationary or relatively stationary, to provide an indication of the patient's environment. Examples of stationary triggers or beacons are provided in U.S. Pat. No. 7,400,928, entitled Methods and Devices For Detection of Context When Addressing A Medical Condition of a Patient, which is herein incorporated by reference in its entirety. By way of example and not limitation, the trigger may be near the patient's bed to indicate that the patient intends to sleep, the trigger may be in the patient's car to indicate that the patient intends to drive, or the trigger may in the patient's kitchen or dining room, indicating that patient intends to eat.

Figure 10:
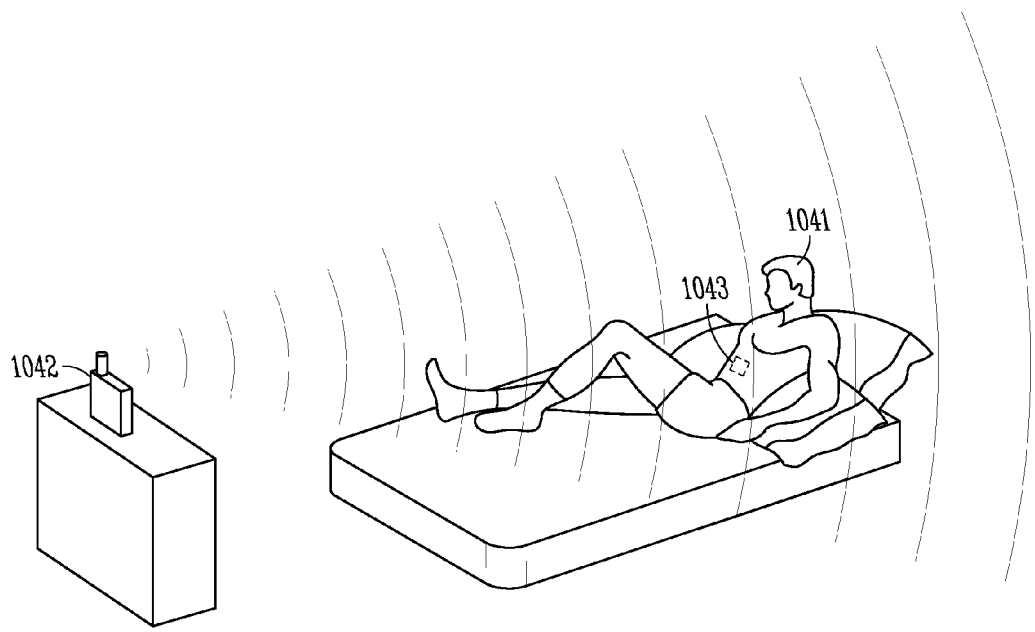
FIGS. 10-11 illustrate embodiments of the present subject matter that detect a signal indicative of a patient's environment.
Figure 11:
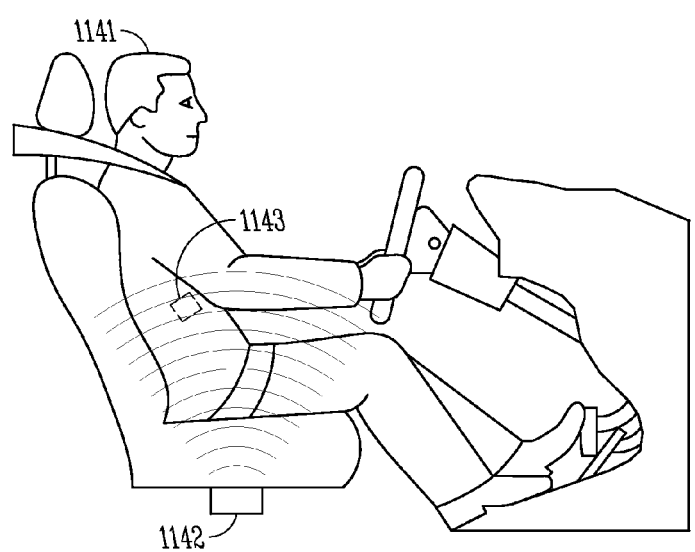

FIG. 10 shows one example of environmental detection. In this example, patient context is detected by proximity sensing. The patient 1041 is lying down in bed and this position may affect the desired therapy. An external device 1042, such as a beacon transmitter is positioned nearby the bed of the patient. When the patient lies down in bed, IMD 1043 becomes within transmission range of the beacon transmitter 1042. The beacon transmitter provides an indication of the patient's environment. Some embodiments use this information to interrupt therapy. In FIG. 11, for example, the patient 1141 is driving a car. The external device 1142 is placed proximal to the seat of the driver and outputs a signal. The IMD 1143 becomes within range of the signals once the patient 1141 sits in the driver's seat. By way of example, the device 1141 may interrupt a therapy for a patient when the patient is in the car.

These context detectors can be implemented with other patient-controlled triggers, such as a magnet. For example, the IMD can be programmed to deliver or interrupt a neural stimulation therapy, in a specific manner, if the IMD detects both a beacon representative of a patient's bedroom and another patient-controlled trigger. For example, the device may be programmed to interpret the combination as an indication that the patient intends to fall asleep for six or more hours allowing the device to temporarily deliver an appropriate therapy during that time, or the device may be programmed to interpret the combination as an indication that the patient intends to stay awake and thus override a normally-scheduled therapy that would occur during the patient's sleep.

Figure 12:
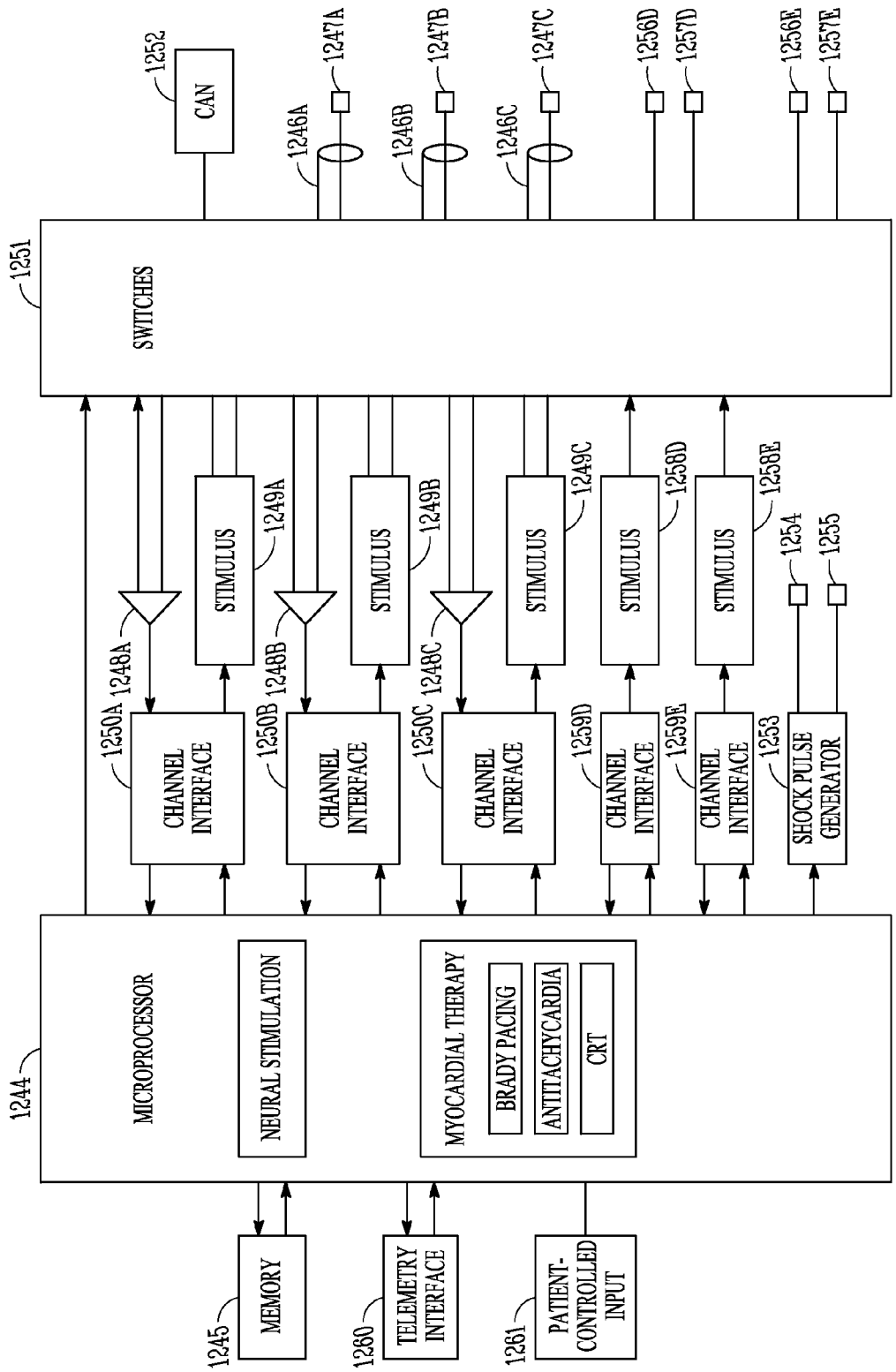
FIG. 12 shows a system diagram of an embodiment of a microprocessor-based implantable device, according to various embodiments.

FIG. 12 shows a system diagram of an embodiment of a microprocessor-based implantable device, according to various embodiments. The controller of the device is a microprocessor 1244 which communicates with a memory 1245 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 1246A-C and tip electrodes 1247A-C, sensing amplifiers 1248A-C, pulse generators 1249A-C, and channel interfaces 1250A-C. Each channel thus includes a pacing channel made up of the pulse generator connected to the electrode and a sensing channel made up of the sense amplifier connected to the electrode. The channel interfaces communicate bidirectionally with the microprocessor, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias. The sensing of these channels can be used to detect cardiac activity for use in synchronizing neural stimulation and for use as feedback in titrating the neural stimulation.

The electrodes of each bipolar lead are connected via conductors within the lead to a switching network 1251 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 1252 or an electrode on another lead serving as a ground electrode. A shock pulse generator 1253 is also interfaced to the controller for delivering a defibrillation shock via a pair of shock electrodes 1254 and 1255 to the atria or ventricles upon detection of a shockable tachyarrhythmia.

Neural stimulation channels, identified as channels D and E, are incorporated into the device for delivering parasympathetic stimulation and/or sympathetic inhibition, where one channel includes a bipolar lead with a first electrode 1256D and a second electrode 1257D, a pulse generator 1258D, and a channel interface 1259D, and the other channel includes a bipolar lead with a first electrode 1256E and a second electrode 1257E, a pulse generator 1258E, and a channel interface 1259E. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links.

The figure illustrates a telemetry interface 1260 connected to the microprocessor, which can be used to communicate with an external device. Also illustrated is a patient-controlled input 1261 to the microprocessor 1244. The therapy routines performed by the microprocessor are configured to respond to the patient-controlled input by, for example, temporarily interrupting the therapy for a defined or programmed period of time, and then automatically restore the therapy when the period of time ends. The illustrated microprocessor is capable of performing neural stimulation therapy routines and myocardial (CRM) stimulation routines. The neural stimulation routines can target nerves to affect cardiac activity (e.g. heart rate and contractility). The neural stimulation routines can include programmed routines for responding to patient-controlled indicators, as disclosed in various embodiments in this document. Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT).

Figure 13:
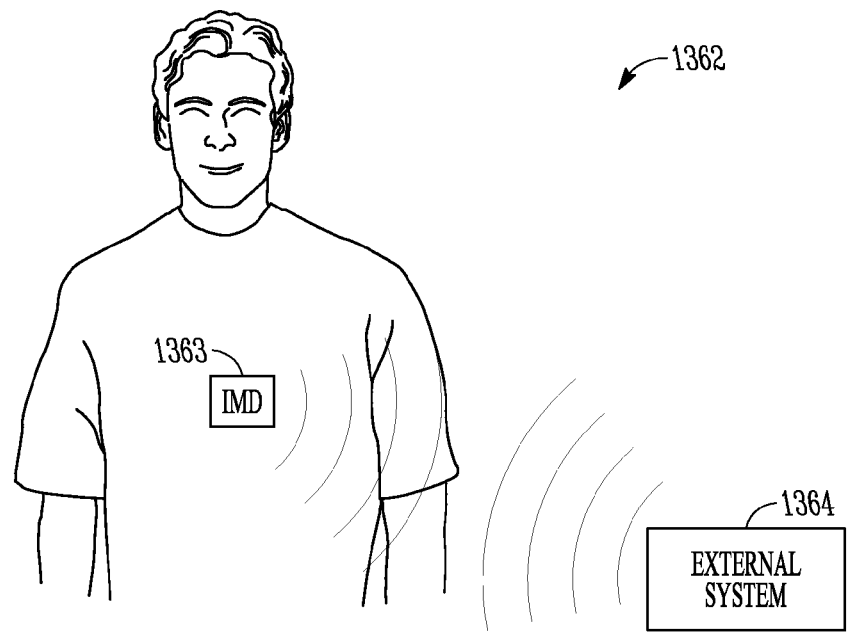
FIG. 13 illustrates a system including an IMD and an external system or device, according to various embodiments.

FIG. 13 illustrates a system 1362 including IMD 1363 and an external system or device 1364, according to various embodiments of the present subject matter. Various embodiments of the IMD include a combination of NS and CRM functions. The IMD may also deliver biological agents and pharmaceutical agents. The external system and the IMD are capable of wirelessly communicating data and instructions. In various embodiments, for example, the external system and IMD use telemetry coils to wirelessly communicate data and instructions. Thus, the programmer can be used to adjust the programmed therapy provided by the IMD, and the IMD can report device data (such as battery and lead resistance) and therapy data (such as sense and stimulation data) to the programmer using radio telemetry, for example. According to various embodiments, the IMD stimulates/inhibits a neural target to affect cardiac activity.

The external system allows a user such as a physician or other caregiver or a patient to control the operation of the IMD and obtain information acquired by the IMD. In one embodiment, the external system includes a programmer communicating with the IMD bi-directionally via a telemetry link. In another embodiment, the external system is a patient management system including an external device communicating with a remote device through a telecommunication network. The external device is within the vicinity of the IMD and communicates with the IMD bi-directionally via a telemetry link. The remote device allows the user to monitor and treat a patient from a distant location. The patient monitoring system is further discussed below.

The telemetry link provides for data transmission from the implantable medical device to the external system. This includes, for example, transmitting real-time physiological data acquired by the IMD, extracting physiological data acquired by and stored in the IMD, extracting therapy history data stored in the IMD, and extracting data indicating an operational status of the IMD (e.g., battery status and lead impedance). The telemetry link also provides for data transmission from the external system to the IMD. This includes, for example, programming the IMD to acquire physiological data, programming the IMD to perform at least one self-diagnostic test (such as for a device operational status), and programming the IMD to deliver at least one therapy.

Figure 14:
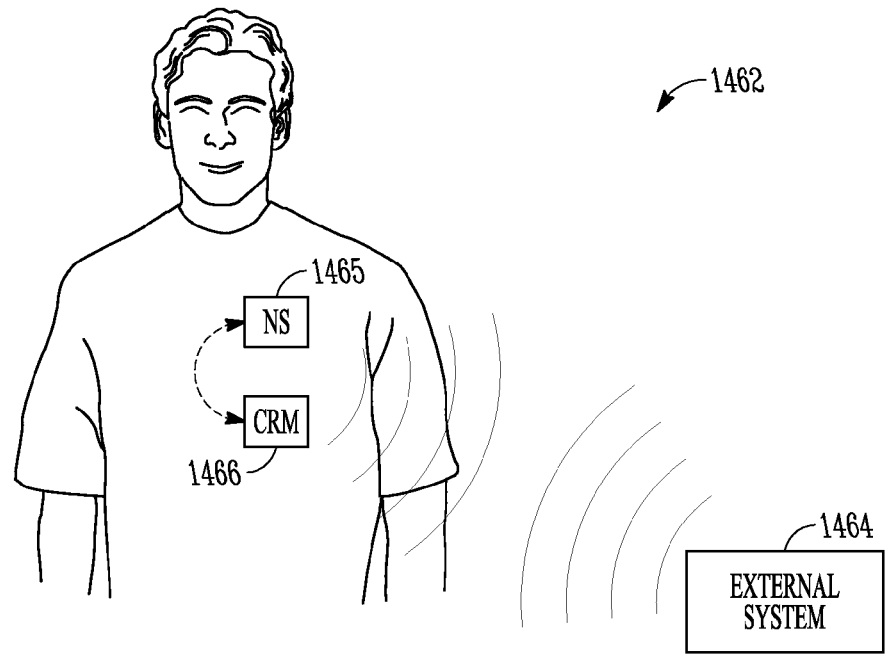
FIG. 14 illustrates a system including an external device, an implantable neural stimulator (NS) device and an implantable cardiac rhythm management (CRM) device, according to various embodiments.

FIG. 14 illustrates a system 1462 including an external device 1464, an implantable neural stimulator (NS) device 1465 and an implantable cardiac rhythm management (CRM) device 1466, according to various embodiments of the present subject matter. Various aspects involve a method for communicating between an NS device and a CRM device or other cardiac stimulator. In various embodiments, this communication allows one of the devices 1465 or 1466 to deliver more appropriate therapy (i.e. more appropriate NS therapy or CRM therapy) based on data received from the other device. The illustrated NS device and the CRM device are capable of wirelessly communicating with each other, and the external system is capable of wirelessly communicating with at least one of the NS and the CRM devices. For example, various embodiments use telemetry coils to wirelessly communicate data and instructions to each other. In other embodiments, communication of data and/or energy is by ultrasonic means. Rather than providing wireless communication between the NS and CRM devices, various embodiments provide a communication cable or wire, such as an intravenously-fed lead, for use to communicate between the NS device and the CRM device. In some embodiments, the external system functions as a communication bridge between the NS and CRM devices.

Figure 15:
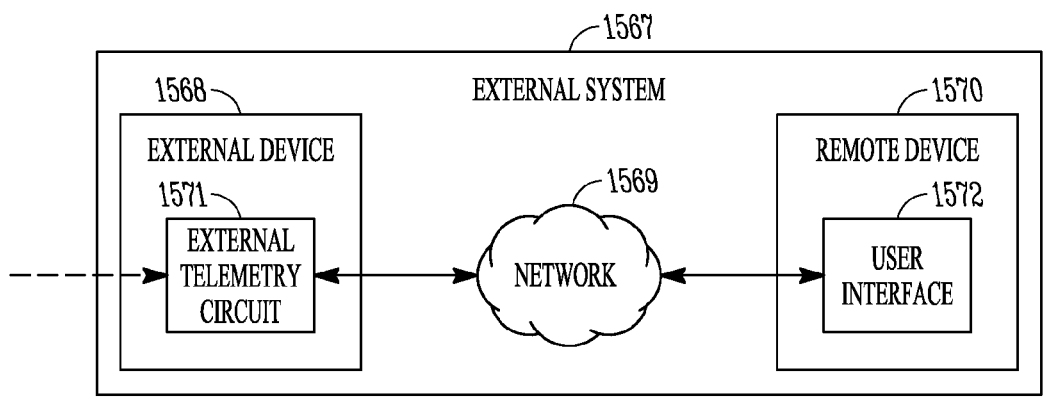
FIG. 15 is a block diagram illustrating an embodiment of an external system.

FIG. 15 is a block diagram illustrating an embodiment of an external system 1567. The external system includes a programmer, in some embodiments. In the illustrated embodiment, the external system includes a patient management system. As illustrated, the external system 1567 is a patient management system including an external device 1568, a telecommunication network 1569, and a remote device 1570. The external device 1568 is placed within the vicinity of an IMD and includes external telemetry system 1571 to communicate with the IMD. Remote device(s) 1570 is in one or more remote locations and communicates with external device 1568 through network 1569, thus allowing a physician or other caregiver to monitor and treat a patient from a distant location and/or allowing access to various treatment resources from the one or more remote locations. The illustrated remote device includes a user interface 1572.

Some system embodiments are configured to allow the patient or physician to go back and retrieve information regarding the triggers that alter therapy. For example, if numerous triggers by the patient interrupt therapy, some embodiments run a report on the overall trigger use. This information can be used to verify that the system is working appropriately.

Some system embodiments modify, over time, the response of the device to a patient trigger over time. The alteration to the response may be automatically modified based on previous episodes and memory of the device. For example, the device response may lag slightly behind the triggered response. By way of another example, a patient controlled trigger may turn therapy on, but the therapy will not turn off until some defined threshold is crossed. In some embodiments, this threshold is based on previous episodes and values stored in the memory of the device.

As will be understood by one of ordinary skill in the art upon reading and comprehending the present subject matter, various embodiments of the present subject matter improve patient acceptance of therapy, maintain efficacious levels of therapy, allow patient flexibility in therapy management, and generally improve the quality of life of the patient who is receiving the NCT. The modules and other circuitry shown and described herein can be implemented using software, hardware, firmware and combinations thereof.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method performed by an implantable medical device to deliver a therapy to a patient, the method comprising:
    delivering the therapy to the patient;
    detecting a therapy interruption trigger that is controlled by the patient;
    automatically interrupting the therapy in response to the detected therapy interruption trigger;
    automatically restoring the therapy after a defined restoration period after the detected therapy interruption trigger;
    counting a number of detected therapy interruption triggers over a defined therapy interruption trigger count period, the counted number of detected therapy interruption triggers over the defined interruption trigger count period being greater than one, and each of the counted number of detected therapy interruption triggers corresponding to an automatic interruption in the therapy; and
    when the counted number of detected therapy interruption triggers over the defined trigger count period reaches a defined number of detected therapy interruption triggers greater than one trigger, automatically interrupting the therapy in response to the detected therapy interruption trigger includes automatically interrupting the therapy until an authorized individual resets the therapy.

2. The method of claim 1, wherein delivering the therapy includes delivering neural stimulation for a cardiovascular therapy.

3. The method of claim 1, wherein automatically interrupting the therapy includes automatically stopping the therapy in response to the detected therapy interruption trigger.

4. The method of claim 1, wherein automatically interrupting the therapy includes automatically adjusting an intensity of the therapy in response to the detected therapy interruption trigger.

5. The method of claim 4, wherein automatically adjusting an intensity of the therapy includes automatically reducing the intensity of the therapy in response to the detected therapy interruption trigger.

6. The method of claim 4, wherein automatically adjusting an intensity of the therapy includes automatically increasing the intensity of the therapy in response to the detected therapy interruption trigger.

7. The method of claim 1, wherein:
    the defined restoration period is a defined time period;
    the method includes using a timer to determine an end of the defined time period; and
    automatically restoring the therapy includes automatically restoring the therapy at the end of the defined time period.

8. The method of claim 1, wherein:
    the defined restoration period is a defined count of a recurring event that is identifiable by the implantable medical device;
    the method includes detecting recurring events and using a counter to determine when a number of recurring events reaches the defined count; and
    automatically restoring the therapy includes automatically restoring the therapy when the number of recurring events reaches the defined count.

9. The method of claim 8, wherein the recurring event is a neural stimulation pulse or a neural stimulation burst.

10. The method of claim 8, wherein the recurring event is a cardiac event within a cardiac cycle.

11. The method of claim 1, further comprising:
    determining an amount of the therapy over a defined therapy window;
    comparing the amount of the therapy over the defined therapy window to a defined therapy amount; and
    changing the response to the detected interruption trigger if the amount of the therapy over the defined therapy window is less than the defined therapy amount.

12. The method of claim 1, wherein detecting the interruption trigger that is controlled by the patient includes detecting a therapy interruption trigger indicative of an environment of the patient.

13. The method of claim 1, further comprising detecting a signal indicative of an environment of the patient, wherein automatically interrupting the therapy includes automatically adjusting the therapy if the detected therapy interruption trigger and the signal indicative of the environment occur together.

14. The method of claim 1, further comprising performing a ladder response to more than one detected therapy interruption trigger, wherein a first detected therapy interruption trigger is associated with a first time period that functions as the defined time period for the first detected therapy interruption trigger and a second detected therapy interruption trigger is associated with a second time period longer than the first time period that functions as the defined period for the second detected therapy interruption trigger.

15. An implantable medical device for implantation in a patient, comprising:
    a neural stimulation circuit configured for use to deliver a neural stimulation therapy to the patient; and
    a controller configured to:
        control the neural stimulator to deliver the neural stimulation therapy;
        detect a therapy interruption trigger that is controlled by the patient;
        automatically interrupt the therapy in response to the detected therapy interruption trigger; and
        automatically restore the therapy after a defined restoration period after the detected therapy interruption trigger,
    wherein the controller includes an override controller configured to:
        count a number of detected therapy interruption triggers over a defined therapy interruption trigger count period, the counted number of detected therapy interruption triggers over the defined interruption trigger count period being greater than one, and each of the counted number of detected therapy interruption triggers corresponding to an automatic interruption in the therapy;
        compare the counted number of detected therapy interruption triggers over the defined trigger count period to a defined number of detected therapy interruption triggers greater than one trigger; and
        automatically interrupt the therapy until an authorized individual resets the therapy when the counted number of detected therapy interruption triggers over the defined trigger count period reaches the defined number of detected therapy interruption triggers.

16. The device of claim 15, wherein the controller is configured to automatically stop the therapy in response to the detected therapy interruption trigger.

17. The device of claim 15, wherein the controller is configured to automatically adjust an intensity of the therapy in response to the detected therapy interruption trigger.

18. The device of claim 15, wherein:
the defined restoration period is a defined time period;
the controller includes a timer configured to determine an end of the defined time period; and
the controller is configured to automatically restore the therapy at the end of the defined time period.

19. The device of claim 15, wherein:
the device includes a recurring event detector, and a counter configured to count the detected recurring events;
the defined restoration period is a defined count of the detected recurring events; and
the controller is configured to determine when the detected number of recurring events reaches the defined count, and automatically restore the therapy when the number of recurring events reaches the defined count.

20. The device of claim 19, wherein the recurring event is a neural stimulation pulse or a neural stimulation burst.

21. The device of claim 19, wherein the recurring event is a cardiac event within a cardiac cycle.

22. The device of claim 15, wherein the controller includes a therapy dose controller configured to determine an amount of the therapy over a defined therapy window, compare the amount of the therapy over the defined therapy window to a defined therapy amount, and change the response to the therapy detected interruption trigger if the amount of the therapy over the defined therapy window is less than the defined therapy amount.

23. The device of claim 15, the controller is configured to perform a ladder response to more than one detected therapy interruption trigger, wherein a first detected therapy interruption trigger is associated with a first time period that functions as the defined time period for the first detected therapy interruption trigger and a second detected therapy interruption trigger is associated with a second time period longer than the first time period that functions as the defined period for the second detected therapy interruption trigger.

* * * * *